United States Patent [19]

Colclough

[11] 4,104,179

[45] Aug. 1, 1978

[54] LUBRICATING AND PETROLEUM FUEL OIL COMPOSITIONS CONTAINING AZOLE POLYSULFIDE WEAR INHIBITORS

[75] Inventor: Terence Colclough, Oxford, Great Britain

[73] Assignee: Exxon Research & Engineering Co., Linden, N.J.

[21] Appl. No.: 653,935

[22] Filed: Jan. 30, 1976

[30] Foreign Application Priority Data

Feb. 14, 1975 [GB] United Kingdom ................ 6354/75

[51] Int. Cl.$^2$ .............................................. C10M 1/48
[52] U.S. Cl. ................... 252/32.7 E; 252/47; 252/47.5
[58] Field of Search .................... 252/32.7 E, 47, 47.5

[56] References Cited

U.S. PATENT DOCUMENTS

| | | | |
|---|---|---|---|
| 2,704,761 | 3/1955 | D'Amico | 252/47.5 X |
| 2,765,289 | 10/1956 | Fields et al. | 252/32.7 E |
| 2,910,439 | 10/1959 | Fields | 252/47 X |
| 3,533,943 | 10/1970 | Papayannopulus | 252/32.7 G |
| 3,634,240 | 1/1972 | O'Halloran | 252/33.6 X |
| 3,816,311 | 6/1974 | Malec | 252/47 X |
| 3,821,236 | 6/1974 | Ripple | 252/47 X |
| 3,839,212 | 10/1974 | McCoy | 252/52 R |
| 3,896,050 | 7/1975 | White | 252/47 X |
| 3,904,537 | 9/1975 | Ripple | 252/47 X |

*Primary Examiner*—Delbert E. Gantz
*Assistant Examiner*—Andrew H. Metz
*Attorney, Agent, or Firm*—F. T. Johmann; R. A. Dexter

[57] ABSTRACT

Azole aminopolysulfides and azine aminopolysulfides are effective as ashless antiwear agents for lubricating oils, particularly when used in combination with an ashless dispersant.

8 Claims, No Drawings

LUBRICATING AND PETROLEUM FUEL OIL COMPOSITIONS CONTAINING AZOLE POLYSULFIDE WEAR INHIBITORS

This invention relates to lubricating oil and petroleum fuel oil compositions which contain certain heterocyclic compounds which confer good anti-wear and good anti-oxidant properties on the lubricating oil or fuel oil.

It is well-known to include anti-wear and anti-oxidants in lubricating oils, the purpose of the anti-wear agent being to inhibit the wear of the metal parts during operation of the engine whilst the anti-oxidant inhibits decomposition of the oil under the operating conditions of the engine thus reducing the increase in oil viscosity. Hitherto metal containing additives especially zinc di-thiophosphates have been used as anti-wear and anti-oxidants in lubricating oils but these suffer from the disadvantage that they are metal containing and tend to produce metal or ash which contaminates the oil.

There has therefore been a need to replace at least part of these ash producing additives by metal free or ashless compounds. Sulphur is known to impart anti-wear properties to lubricating oils and there have been many suggestions to incorporate sulphur containing compounds into lubricating oils including, for example sulphenamides of heterocyclic benzothiazyl sulphenamides as described in U.S. Pat. No. 2,669,544.

We have now found that a certain group of compounds containing polysulphide groups are effective ashless anti-wear agents in lubricating oils and that these compounds impart improved lead corrosion and anti-wear properties to lubricating oils as compared with the corresponding monosulphides.

The invention therefore provides a lubricating oil or petroleum fuel oil composition comprising (i) a lubricating oil or a petroleum fuel oil (ii) an azole amino polysulphide or an azine amino polysulphide of the structure:

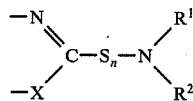

where the group

forms part of a 5-membered azole heterocyclic ring or a 6-membered ring; $n$ is at least 2, X is O, S or —NR$^3$ is H or a hydrogen- and carbon-containing group and R$^1$ and R$^2$ which are the same or different are either hydrogen atoms or hydrogen- and carbon-containing groups or they are part of a hydrogen- and carbon-containing ring and (iii) an ashless dispersant.

Certain of the polysulphides used in the composition of the present invention have been proposed as rubber accelerators but it is believed that their use as additives in lubricating or fuel oils is new and we have found that their use gives rise to improved anti-wear properties with less copper and lead corrosion than that obtained with other similar compounds. It is preferred that in the polysulphide which is added to the fuel oil or lubricating oil $n$ is 2, i.e. that the polysulphide is an azole amino disulphide or an azine amino disulphide.

R$^1$ and R$^2$ may be part of a hydrogen- and carbon-containing ring, e.g. a morpholino ring, a piperidino or a piperazino ring or they may be separate hydrogen- and carbon-containing groups or hydrogen atoms. Although it is possible for both R$^1$ and R$^2$ to be hydrogen atoms it is preferred that at least one of them is hydrogen- and carbon-containing group.

When they are not hydrogen atoms then R$^1$ and R$^2$ are preferably hydrocarbyl groups i.e. contain no atoms other than hydrogen and carbon, although R$^1$ and R$^2$ may if desired contain other atoms, e.g. oxygen or nitrogen atoms.

The groups R$^1$ and R$^2$ can be aliphatic or aromatic, e.g. they may be alkyl, aryl, aralkyl or alkaryl groups. If alkyl, the groups R$^1$ and R$^2$ preferably contain from 1 to 25 carbon atoms and they may be straight or branched chain. If alkaryl or aralkyl the groups R$^1$ and R$^2$ preferably contain from 1 to 18 carbon atoms in the alkyl part of the chain which may be straight or branched.

Primary and secondary amines from which the

portion in the structural formula can be derived are for example ethylamine, cyclohexyl amine, n-butyl amine, s-butylamine, t-butylamine, t-octyl amine, dodecylamine, diethylamine, di-n-amylamine, di-hexylamine, di-cyclohexyl amine, ethylene diamine, benzylamine, hexamethylenimine, aniline, toluidine, diphenylamine, alkylated diphenylamine, morpholine, piperidine, piperazine and dimethylmorpholine.

The group

forms part of a 5-membered ring in which case the sulphide is an azole amino sulphide or forms part of a 6-membered ring in which case the sulphide is an azine amino sulphide.

Examples of 5-membered rings are the:

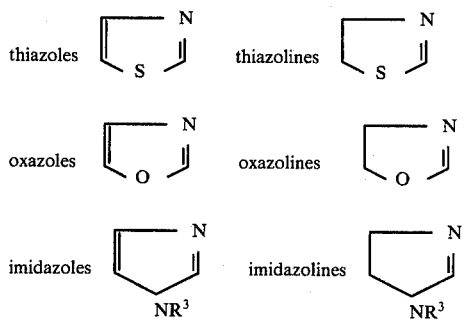

where R$^3$ is H or a hydrogen and carbon containing group. Further examples are

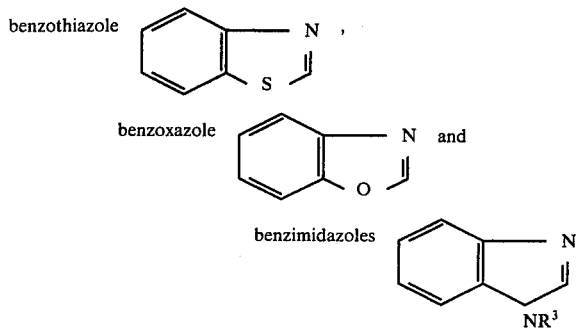

where $R^3$ is H or a hydrogen- and carbon-containing group.

Examples of 6-membered rings are 4H-1:3 thiazine and 6H-1:3 thiazine i.e.

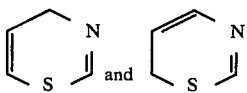

and the corresponding ozazines 4H-1:3 oxazine and 6H-1:3 oxazine i.e.

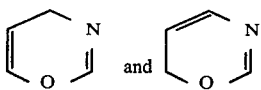

Further examples are the corresponding benz-1:3 thiazines and benz-1:3 oxazines.

In the case of the imidazolines, imidazolines and benzimidazolines $R^3$ is preferably hydrogen but it may if desired be a hydrogen- and carbon-containing group, e.g. a hydrocarbyl group such as an alkyl group e.g. a methyl, ethyl or butyl group.

The above mentioned 5- or 6-membered rings may if desired be substituted. The substituents may include polar substituents e.g. keto, amino, hydroxy, nitro, ester or sulphide groups, or they may include hydrocarbyl groups, or they may include substituted hydrocarbyl groups. The substituent hydrocarbyl groups may also in turn if desired contain substituent polar groups such as those mentioned above. Suitable substituted ring compounds are e.g. hydroxy thiazoles, thiazolenes and amino-thiazoles.

Di-sulphides can be made by reacting an azole or azine mercaptan with a primary or secondary amine and a sulphur halide, e.g. sulphur dichloride. Thus, for example:

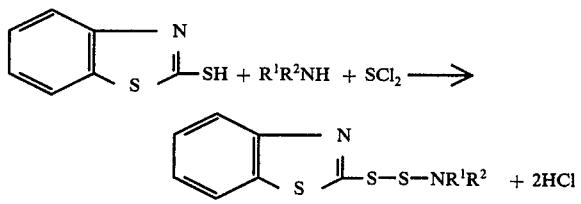

It should be noted that some heterocyclic compounds from which the azole or azine amino polysulphides of this invention can be derived exist in tautomeric form.

Thus, for example, rhodanine is a suitable compound from which the azole amine sulphides or azine amine sulphides can be obtained.

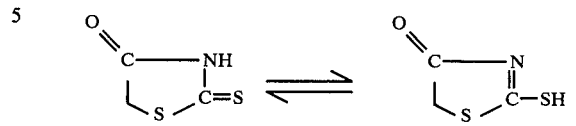

Another example is mercapto benzothiazole:

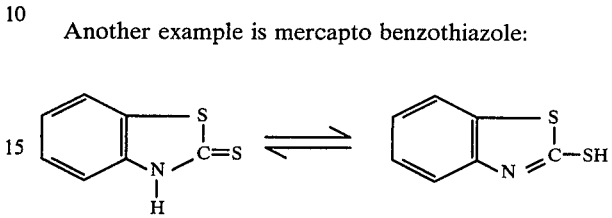

However, the most preferred sulphides to be used in the compositions of this invention are the disulphides derived from mercaptobenzothiazole, or from mercapto thiazole.

The azole amino polysulphide or azine amino polysulphide can be present in a lubricating oil as a minor proportion by weight, where it acts as an anti-oxidant and an anti-wear agent. It can also be present in a petroleum fuel oil, e.g. diesel fuel, as a minor proportion by weight. The polysulphides may be used as a total replacement for conventional anti-wear agents and anti-oxidants such as the zinc dialkyldithiophosphates or as a partial replacement thereof enabling one to obtain corresponding or improved anti-wear properties at lower levels of zinc and phosphorous in the oil. Thus certain lubricating or fuel oils may contain both a polysulphide of the present invention together with a zinc dialkyldithiophosphate.

In certain oils it is necessary to incorporate metal containing additives such as the calcium and magnesium sulphonates and phenates which may be neutral or highly basic. The presence of these metallic compounds leads to the formation of ash in the oils which increases engine wear and thus it has been necessary to increase the amount of anti-wear agent (usually a zinc dialkyldithiophosphate) to compensate but this of course has the disadvantage that the anti-wear agent itself is metal containing. The use of the polysulphides of the present invention in oils of this type has been found to achieve the desired anti-wear properties without unduly increasing the zinc dialkyldithiophosphate content.

The solubility in oil of the polysulphides depends of course upon the particular structure of the polysulphide and also the nature of the oil. Certain polysulphides are solid compounds but are soluble in zinc dialkyldithiophosphates thus the combination of the two provides a fluid which may readily be incorporated in an oil. We have also found that the addition of a small amount of an alkyl phenol maintains the solubility of the polysulphide at lower temperatures. This technique is especially useful when using one of our preferred polysulphides which is morpholino benzothiazole disulphide which is normally a solid. Typical formulations may contain from 70 to 90 parts of the zinc dialkyldithiophosphate and 15 to 25 parts by weight of the polysulphide preferably with from 5 to 15 parts of an alkyl phenol whose alkyl group preferably contains at least six carbon atoms such as nonyl phenyl. These formulations are fluids which can readily be incorporated into oils to give the advantages described above of the antioxidant properties of the zinc dialkyl-dithiophosphate and improved anti-wear properties at lower zinc and phosphorous levels.

The polysulphides used in the compositions of the present invention may also be based on the thiadiazole nucleus which may be the 1,2,4 or 1,3,4 thiadiazole rings. Thus the polysulphides may be of the general formula:

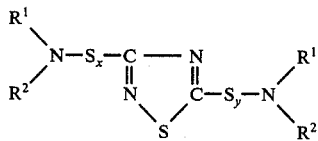

or

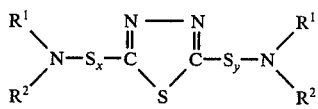

Where at least one of $x$ and $y$ is at least 2 and $R^1$ and $R^2$ are as defined previously.

The ashless dispersants used in the lubricating or fuel oil compositions of the present invention may be any of the new well-known ashless dispersants. Examples of suitable dispersants include the lubricant and fuel additives derived from hydrocarbon substituted succinic anhydride, e.g. polyisobutenyl-succinic anhydride, with compounds containing both an amine group and a hydroxy group which have been suggested in for example, U.S. Pat. No. 3,272,746 which teaches the reaction of ethanolamine and diethanolamine, as well as various hydroxyalkyl substituted alkylene amines, such as N-(2-hydroxyethyl) ethylene diamine, N,N¹bis (2-hydroxyethyl) ethylene diamine, with alkenylsuccinic anhydride to obtain ashless dispersants for lube oil. Alternative compounds in which a hydroxy amine, such as diethanolamine, is reacted with a long chain alkenylsuccinic anhydride to form a mixture of esters and amides, wherein some of the diethanol-amine reacts through a hydroxy group to give an ester linkage, while another portion of the diethanolamine forms an amide linkage as in U.S. Pat. No. 3,324,033 may be used. Other examples are given in U.S. Pat. No. 3,364,001 which teaches a tertiary alkanolamine reacted with an alkenylsuccinic anhydride to form an ester useful as a gasoline additive. U.S. Pat. No. 3,448,049 teaches dispersants, in lubricants and fuels by esterifying alkenylsuccinic anhydride with a hydroxy compound made by reacting an alkanolamine with an unsaturated ester, amide or nitrile. U.S. Pat. No. 3,630,904 teaches reacting a hydroxy amine, with both short and long chain dicarboxylic acid. U.S. Pat. No. 3,484,374 teaches the polymeric condensation products of polycarboxylic acid or anhydride with various alkanolamines such as aminoethylethanolamine, N-methyldiethanolamine, etc. United Kingdom specification No. 809,001 teaches corrosion inhibitors comprising a multiple salt complex derived from the reaction product of hyrocarbyl substituted dicarboxylic acids and hydroxy amines (including 2-amino-2-methyl-1,3-propane-diol (AMP) and tris hydroxy methylaminomethane hereafter designated THAM) further complexed with mono- and polycarboxylic acids.

Any of these dispersants may be used and they may be borated or admixed with borate esters to give a further improvement in anti-corrosion properties.

The lubricating oil may be any animal, vegetable or mineral oil, for example example, petroleum oil fractions ranging from naphthas to spindle oil to SAE 30, 40 or 50 lubricating oil grades, castor oil, fish oils or oxidised mineral oil. Alternatively the oil may be a synthetic ester lubricating oil for example diesters such as di-octyl adipate, dioctyl sebacate, didecyl azelate, tridecyl adipate, didecyl succinate, didecyl glutarate and mixtures thereof. Alternatively, the synthetic ester can be a polyester such as that prepared by reacting polyhydric alcohols such as trimethylol propane and pentaerythritol with monocarboxylic acids such as butyric acid, caproic acid, caprylic acid and pelargonic acid to give the corresponding tri- and tetra-esters.

Also, complex esters may be used as base oils such as those formed by esterification reactions between a dicarboxylic acid, a glycol and an alcohol and/or a monocarboxylic acid.

The preferred quantity of polysulphide in the lubricating oil is between 0.01 and 10%, e.g. between 0.1 and 5% by weight based on the total weight of oil plus polysulphide.

Other additives, in addition to dispersants may be included depending upon the use for the oil. For example formulations for lubricating oils may contain additional anti-oxidants (e.g. phenolic compounds), anti-rust additives and other anti-corrosion additives, viscosity index improvers, detergent inhibitors and flow improvers.

The polysulphides and ashless dispersant formulation of the present invention may be in the form of a concentrate in oil which is supplied for blending with bulk lubricating oils. In this situation the concentrate may contain the other additives and may contain from 15% to 25% by weight of the polysulphide with the other components being in the same ratio to the polysulphide as is described above.

The polysulphides may also be used in automatic transmission fluids in which many component additives which are typically blended into the lubricating mineral oil at the following range of treating levels:

| Components | Concentration Range, Vol.% |
|---|---|
| V.I. Improver | 1–15 |
| Corrosion Inhibitor | 0.01–1 |
| Oxidation Inhibitor | 0.01–1 |
| Dispersant | 0.5–10 |
| Pour Point Depressant | 0.01–1 |
| De-Emulsifier | 0.001–0.1 |
| Anti-Foaming Agent | 0.001–0.1 |
| Anti-Wear Agent | 0.001–1 |
| Seal Swellant | 0.1–5 |
| Friction Modifier | 0.01–1 |
| Mineral Oil | 0.01–1 |

As indicated above, the corrosion inhibitor or at least part thereof may be the polysulphide used in composition of the present invention. The treat rate is obvious from the above typical formulations which has been blended for the ATF lubricant. One advantage of using the composition of the invention as ATF lubricants, is that it leads to a reduction in the copper corrosiveness of commercial ATF lubricants.

The present invention is illustrated but in no way limited by the following examples.

EXAMPLE 1

Preparation of morpholino benzothiazole disulphide t-butyl amino benzothiazole (480 g, 2 moles) was heated with sulphur (649 g, 2 g atoms) and morpholine (180 g) in ethanol (1700 ml) for 2 hours at 75°–80° C. The reaction mixture, which contained much solid was cooled, solvent stripped, filtered and washed with petroleum ether to remove morpholine. The product, morpholino benzothiazole disulphide (540 g) contained sulphur 34.5%, nitrogen 9.7% (theory, sulphur 33.7. nitrogen 9.9).

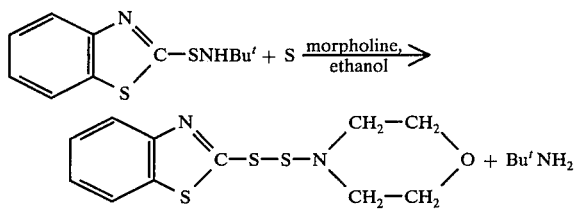

This morpholino benzothiazole sulphide was added to a 10W-30 lubricating oil containing a conventional ashless dispersant and a V.I. improver to give a Petter W-1 bearing weight loss (BWL) of 65 mg at 1 wt.% concentration. A similar lubricating oil composition without any disulphide gave a BWL of about 4,000 mg on the same test. It is clear by these results that the disulphide has good anti-wear properties.

The results of bench tests using the same 10W-30 lubricating oil containing a conventional ashless dispersant and a VI improver was as follows:

| Additive (wt. % in 10W-30 oil) | 4 Ball Wear Scar (120 Kg) (min) Diameter (mm) | Lead Corrosion (mg wt. Loss) |
|---|---|---|
| Nil | 3.0 | 6000 |
| Morpholino benzothiazole disulphide (0.5) | 1.9 | 22 |

The morpholino benzothiazole disulphide was a solid which was found to be soluble in a highly paraffinic base oil of 150 SSU viscosity at 210° F at between 70° and 80° C although slight sedimentation occurred at 20° C. It was found however that 15 parts of the product were soluble in 75 parts of zinc dialkyl-dithiophosphate and that a clear mobile liquid was retained at temperatures as low as 0° C when 10 parts of nonyl phenol were added to this solution.

EXAMPLE 2

The anti-wear and corrosion properties of the morpholino benzothiazole disulphide prepared in Example 1 were compared to those of morpholino benzothiazole monosulphide. Equimolar quantities of the two compounds were incorporated into separate samples of a highly refined paraffinic lubricating oil containing 6% by weight of a conventional polyamine type ashless dispersant. These oils were then subjected to the standard 4 ball wear scar diameter test and the SOD test in which standard samples of copper and lead are attached to a stirrer in a vessel containing the oil sample which is then subjected to air oxidation by blowing for 20 hours at 325° F and measuring the weight loss of the metal.

An oil containing no sulphide but 1.0% by weight of a zinc dialkyl-dithiophosphate (ZDDP) was also subjected to the same four ball test.

The results were as follows:

| Additive | 4 Ball Wear (120 Kg/1 min) Scar | Lead Weight Loss in SOD test (mg) |
|---|---|---|
| Morpholino benzothiazole disulphide 0.83 wt.% | 1.65 | 2 |
| Morpholino benzothiazole monosulphide 0.75 wt.% | 2.05 | 310 |
| ZDDP (1.0%) | 2.50 | |

EXAMPLE 3

120 grams of the N-tertiary-butyl benzothiazole sulphenamide was heated with 16 grams of sulphur and 110 grams of the $C_{13}$ tertiary alkylamine (Primene 81-R) to 100° C, the solids dissolved and the volatiles were then removed at 400 millimeters pressure. Solids formed on cooling and the liquid fraction was separated by filtration to yield 166 grams of a liquid product containing 21.6% by weight of sulphur and 7.0% by weight of nitrogen. The theoretical amounts for the thiosulphenamide are 23.0% by weight of sulphur and 7.6% by weight of nitrogen. These figures suggest that the liquid fraction was predominantly of the formula:

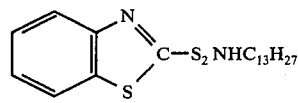

and 1.19% by weight of the compound (being equimolar to the quantities used in Example 2) was incorporated into the lubricating oil of Example 2 containing 6% by weight of a conventional polyamine dispersant. This oil was then subjected to the four ball and SOD tests to give a wear scar of 1.85 millimeters and a lead weight loss of 1 milligram. A similar composition containing 1% by weight of this compound gave a wear scar of 1.80 millimeters.

The performance of this compound was compared to that tertiary-butyl amino benzothiazole monosulphide by incorporating 0.66% by weight (an equimolar amount of the amount of compound used above) and into the same oil and subjecting the oil to the four ball and SOD tests to give a wear scar of 2.45 millimeters and a lead weight loss of 4608 milligrams.

When 0.5% by weight of tertiary-butyl amino benzothiazole monosulphide was incorporated into the oil of Example 1 the wear scar in the four ball test was found to be 2.5 and the lead corrosion loss 2200 milligrams.

EXAMPLE 4

The morpholino benzothiazole disulphide of Example 1 was included in a 10W/30 lubricating oil containing 6% by weight of a conventional ashless dispersant and 5% by weight of a viscosity index improver (20% by weight active ingredient) and the oil subjected to the standard Volvo B-20 Cam and Tappett test. It was found that only 0.2% by weight of the morpholino benzothiazole disulphide based on the weight of the oil was required to achieve a pass in this test whilst 0.7% of a zinc dialkyldithiophosphate was required to achieve a pass.

EXAMPLE 5

A 10W/30 lubricating oil containing 6.0% by weight of a conventional dispersant, 7.7% of a viscosity index improver (20% by weight active ingredient) and 0.5% by weight of a basic magnesium sulphonate required 1.4% by weight of a zinc dialkyldithiophosphate to pass the Volvo B-20 Cam and Tappett test whilst a similar oil containing 0.9% by weight of the zinc dialkyldithiophosphate and 0.2% by weight of the morpholino benzothiazole disulphide of Example 1 passed this test.

I claim:

1. An oil composition comprising a major amount of lubricating oil, a minor but at least a metal wear inhibiting amount of an azoleamino polysulfide or an azine aminopolysulfide of the structure:

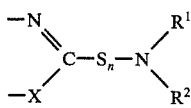

where the group

forms part of a 5-membered azole heterocyclic ring or a 6-membered azine heterocyclic ring, $n$ is at least 2, X is O, S, or $NR^3$ where $R^3$ is H or a lower alkyl group and $R^1$ and $R^2$ which are the same or different are hydrogen, a hydrocarbyl group containing from 1 to 25 carbons or one part of a ring of the class consisting of morpholino, piperidino and piperazino and a minor but at least dispersing amount of a lubricating oil ashless dispersant.

2. An oil composition according to claim 1 containing in addition a minor but at least oxidation-inhibiting amount of a zinc dialkyldithiophosphate and said polysulfide is morpholino benzothiazole disulfide.

3. An oil composition according to claim 1 in which $n$ is 2, $R_1$ and $R_2$ are hydrogen or an alkyl group and said polysulfide is present in an amount between 0.01 to 10% by weight based on the total weight of oil plus polysulfide.

4. An oil composition according to claim 2 containing from 15 to 25 parts by weight of the polysulfide for every 70 to 90 parts by weight of said zinc dialkyldithiophosphate.

5. An oil composition according to claim 4 containing from 5 to 15 parts by weight of an alkyl phenol for each 15 to 25 parts by weight of the polysulfide.

6. An oil composition according to claim 3 in which the polysulfide is present in an amount from 0.1 to 5.0% by weight of the oil plus polysulfide.

7. An oil composition comprising a major amount of a lubricating oil and a minor but at least metal wear inhibiting amount of an azole polysulfide of the general formula:

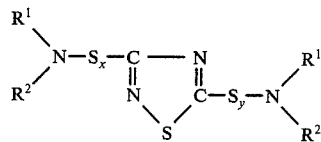

wherein at least one of X and Y is at least 2, and $R^1$ and $R^2$ which are the same or different are hydrogen, a hydrocarbyl group containing from 1 to 25 carbons or one part of a ring of the class consisting of morpholino, piperidino and piperazino.

8. An oil composition comprising a major amount of a lubricating oil and a minor but at least metal wear inhibiting amount of an azole polysulfide of the general formula:

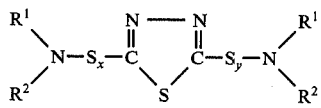

where at least one of $x$ and $y$ is at least 2 and $R^1$ and $R^2$ which are the same or different are hydrogen, a hydrocarbyl group containing from 1 to 25 carbons or one part of a ring of the class consisting of morpholino, piperidino and piperazino.

* * * * *